United States Patent [19]

Perez Pascual et al.

[11] Patent Number: 5,138,092
[45] Date of Patent: Aug. 11, 1992

[54] PROCESS FOR OBTAINING SEC-BUTYL ACRYLATE

[75] Inventors: Miguel A. Perez Pascual; Fernando Albertos de Benito, both of Madrid, Spain

[73] Assignee: Compania Espanola de Petroleos, S.A. Cersa, Madrid, Spain

[21] Appl. No.: 659,965

[22] Filed: Feb. 22, 1991

[30] Foreign Application Priority Data

Mar. 5, 1990 [ES] Spain .................................. 9000646

[51] Int. Cl.$^5$ ............................................. C07C 69/52
[52] U.S. Cl. ................................................... 560/205
[58] Field of Search ........................................ 560/205

[56] References Cited

FOREIGN PATENT DOCUMENTS 0268999 1/1988 European Pat. Off. .

Primary Examiner—Paul J. Killos
Attorney, Agent, or Firm—Darby & Darby

[57] ABSTRACT

It comprises reacting, both continuously and discontinuously, acrylic acid and 1-butene in the presence of an ionic exchange resin that contains sulfonic acid groups, carrying out the reaction at a temperature between 50° and 120° C., at a pressure between 10 and 30 kg/cm$^2$, for a reaction or contact time between 0.5 and 4 hours and using a olefin/acrylic acid molar ratio between 0.3 and 10.

The sec-butyl acrylate obtained is useful in polymerization processes yielding very hard polymers with a high thermal resistance and high resistance to hydrolysis.

FIG. 1 represents a graph of the effect of the olefin/acrylic acid ratio over the conversion of acrylic acid.

5 Claims, 2 Drawing Sheets

PROCESS FOR OBTAINING SEC-BUTYL ACRYLATE

TECHNICAL FIELD OF THE INVENTION

The present invention fits in the technical field of the production of acrylates and specifically of the production of sec-butyl acrylate by adding 1-butene to acrylic acid, in the presence of an ionic exchange resin that contains sulfonic acid groups.

PRIOR ART

The production of esters in general and of acrylates in particular, in the presence of acid catalysts, is a process which is perfectly described and established. Among the known methods are the esterification of the acid with alcohol and adding the olefin corresponding to carboxylic acid.

This second process has important advantages over the conventional esterification of alcohol, especially if there is a cheap source of olefins, since the raw material has a marked incidence on the price of the final product. Likewise, the fact that water in this case is not a reaction product, which facilitates the purification of the product and the recovery of the non-converted reacting agents is also very important in the savings of the process.

A difference to be emphasized between the two processes is that, since the reaction takes place following different reaction mechanisms, the use of one or the other makes it possible to obtain more easily different types of ester. Following the classic esterification process, only the obtaining of alkyl-primary radical esters has been carried out on the industrial level due to the difficulty existing to esterify secondary and even more so tertiary alcohols. On the contrary by means of the process of adding the olefin to the acid, alkyl-tertiary radical esters are obtained more easily, with certain difficulty the corresponding alkyl-secondary ones and the synthesis of alkyl-primary esters is very difficult. This type of products obtained by adding an olefin to acrylic acid and which have in common the presence of ramification in the alkyl chain have some excellent market prospects because they are polymerizable just like the other esters of acrylic or metacrylic acid, pure as well as forming part of a copolymer with other esters and they give rise to a very hard polymer with high thermal resistance and high resistance to hydrolysis.

Among the methods of adding olefins to carboxylic acids, two big groups may be distinguished. The first, called "homogeneous processes" hereinafter, is formed by all those processes in which the reagents and catalyst are in the same phase, generally liquid. The second group, called "heterogeneous processes", consists of all those systems in which the catalyst and reacting agents are in different phases, normally solid catalysts and liquid or gas reacting agents.

A characteristic common to the homogeneous processes is the use of a strong acid as a catalyst, sulfuric acid being the one used most extensively as is described in patent BP 814,360 for the production of terc-butyl metacrylate from metacrylic acid and isobutylene. Given the nature of this type of acid products, use thereof entails a problematic recovery of the catalyst, the occurrence of colored by-products that complicate purification of the ester and the existence of corrosion of the reaction equipment.

Due to the cited factors, there is great interest in developing a heterogeneous process that using a solid catalyst, sufficiently active and selective for adding, avoids the problems of recovery, coloring of the reaction medium and corrosion, associated with homogeneous processes.

In order to carry out direct esterification of olefins various types of catalysts have been described, as for example in the U.S. Pat. No. 3,076,840 teaches an esterification process of tertiary olefins with carboxylic acids in the presence of polyvalent metal silicates of Group III treated with HF. In another U.S. Pat. No. 4,293,499 a method of producing esters from monoolefins and carboxylic acids at a temperature of 100°-400° C. and using a solid catalyst composed of 5-sulfoisophthalic acid in a support that has a surface area between 1 and 1000 $m^2/g$ is included.

The ionic exchange resins containing sulfonic groups have been used to produce olefin esters. U.S. Pat. No. 3,037,052 describes a process of these characteristics in which the reaction is carried out using tertiary and secondary olefins at a broad range of temperatures. In the case of the reaction with secondary olefins and more specifically n-butenes with acrylic acid to obtain sec-butyl acrylate, the product object of the present invention, the conditions used do not permit high degrees of conversion of acrylic acid to be reached, which, due to its boiling point close to that of the corresponding acrylate, along with the fact of having to carry out distillation at a reduced pressure due to the parallel process of polymerizaton, gives rise to a complex purification scheme and recycling of the non-converted acid or to substantial losses of the reagent that make the process economically unfeasible.

More recently patent EP 0268999 A teaches a method of preparing terc-butyl metacrylate from metacrylic acid and isobutylene in the presence of a commercial ionic exchange resin containing sulfonic acid groups and where the undesirable polymerization reactions of the olefin are minimized by means of the appropriate selection of the values of the operation variables.

In view of all of the above, the use of heterogeneous catalysts has some excellent prospects to effect direct esterification of olefins and in particular, cationic exchange resins offer important advantages over homogeneous catalysts in the direct esterification of olefins with carboxylic acids.

SUMMARY OF THE INVENTION

The present invention describes a process of producing sec-butyl acrylate from acrylic acid and 1-butene, in the presence of an ionic exchange resin which contains sulfonic acid groups.

The reaction may be carried out under a wide range of conditions (temperature, olefin/acid molar ratio, contact times) using a continuous system as well as a discontinuous system. The reaction conditions must be suitable to simultaneously obtain a high conversion of acrylic acid and a high selectivity of sec-butyl acrylate, due to the marked incidence of both factors on the purification process. Following said process it is feasible to obtain a sec-butyl acrylate apt for subsequent polymerization, by means of using a simple purification scheme.

DESCRIPTION OF THE INVENTION

The reaction of olefin with acrylic acid is carried out in the presence of a cationic exchange resin which contains sulfonic acid groups. Said resin must be macroporous and have a BET surface area between 20 and 100 m$^2$/g, a maximum pore diameter of 1000Å, a porosity between 20 and 80% and an ionic exchange capacity between 0.5 and 3 m eq/l. Commercially available products which combine the above mentioned characteristics and which may be used to carry out the reaction are Lewatit SPC118, Amberlist 15, Dowex MSC-1, Serdolit Red and others of a similar nature.

These cationic exchange resins can be used both in anhydrous and hydrated form, preferentially effecting dehydration prior to the use thereof in reaction, following any known method and preferentially azeotropic distillation or washing with a dried polar solvent.

The reaction is carried out in liquid phase, in discontinuous as well as continuous equipment, provided with the corresponding feed systems of reacting agents, reactor and product processing. With regard to the reactor, the reaction can be effected in a stationary bed as well as in a continuous or discontinuous stirring tank.

The operating conditions to carry out the reaction must be kept within a working range in order to ensure the obtaining of high conversion and selectivity of the desired product.

The reaction temperature must be high enough to reach a suitable conversion and it is a function of the olefin used. Normally it varies between 50° and 120° C. and preferably between 80° and 110° C. The maximum working temperature is 120° C. due to problems of thermal stability of the resin.

The pressure must be the one necessary to keep the reaction mixture in liquid phase. Obviously the minimum working pressure is again a function of the reacting olefin. The pressure normally used is between 10 and 30 kg/cm$^2$.

The olefin/acrylic acid molar ratio has a big influence on the conversion and selectivity obtained in the reaction. A low olefin/acid molar ratio causes a reduction of conversion of the acid, but increases the selectivity of the process, minimizing the polymerization of the starting olefin. An olefin/acrylic acid ratio between 0.3 and 10 is usually used and preferably between 1 and 5.

When the esterification reaction is carried out discontinuously, the reaction time varies between 0.5 and 4 hours, depending on the temperature and other reaction conditions used. If a continuous scheme is used to manufacture the acrylate, the contact time used is in the same range as that used in the discontinuous option.

The product of the esterification reaction consists of the derived acrylate, the corresponding unreacted olefin, acrylic acid in very low proportions and a certain amount of heavy olefin produced by oligomerization of the starting olefin. When the reaction is carried out under suitable operating conditions, the amount of acrylic acid and heavy olefins is reduced, given the high conversion and selectivity of the process. In any case whenever the above is fulfilled, these components are easily separable, using a degasification and recycling for the unreacted olefin, neutralization and washing with water for the small percentage of residual acrylic acid and distillation under reduced pressure to eliminate the heavy olefins and purify the sec-butyl acrylate produced.

| Legends: | |
|---|---|
| (a) | Acrylic acid conversion (%.) |
| (b) | Reaction time (hr.) |
| (c) | Temperature 90° C. |
| —.— | Molar ratio 3/1 |
| —*— | Molar ratio 1.5/1 |
| — — | Molar ratio 5/1 |

Figure 2:
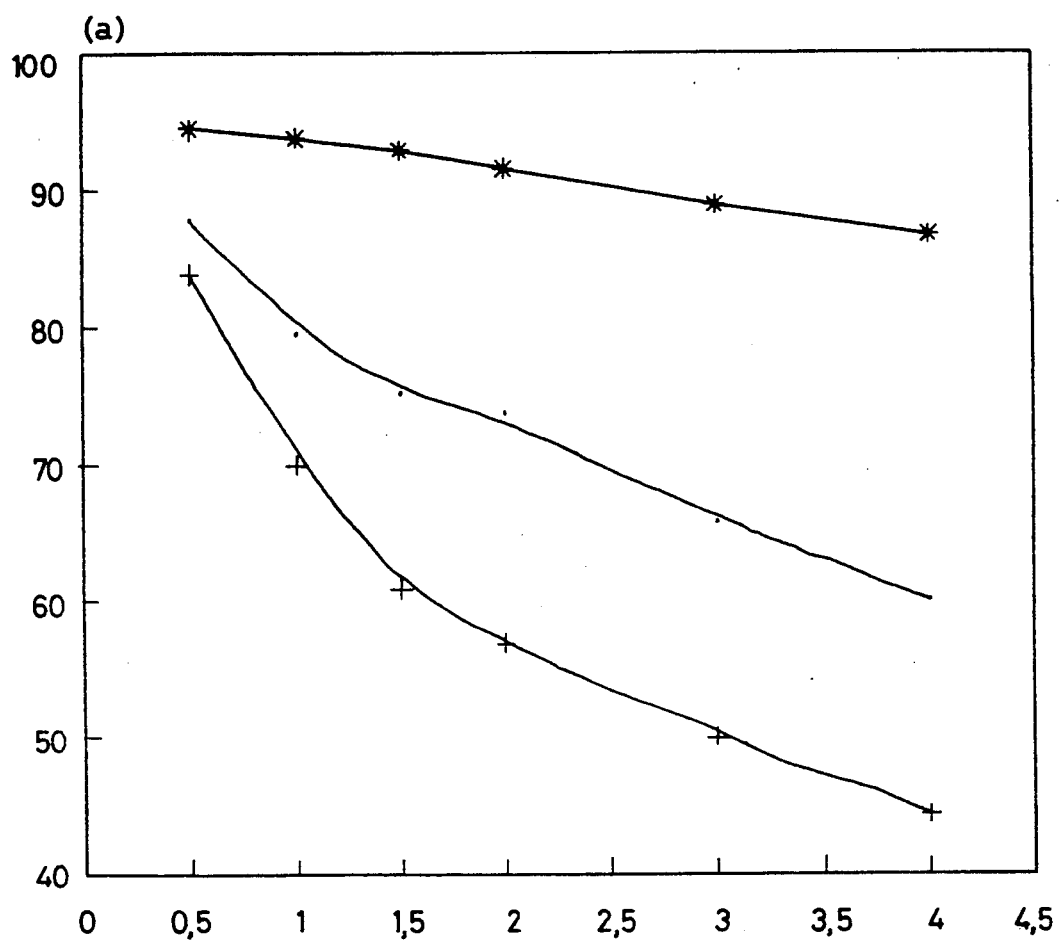

FIG. 2: Graph which represents the effect of the olefin/acrylic acid ratio on selectivity of acrylates.

| Legends: | |
|---|---|
| (a) | Selectivity of acrylates (%.) |
| (b) | Reaction time |
| (c) | Temperature 90° C. |
| —.— | Molar ratio 3/1 |
| —*— | Molar ratio 1.5/1 |
| — — | Molar ratio 5/1 |

EMBODIMENTS OF THE INVENTION

The following non-restrictive examples illustrate the present invention:

EXAMPLE 1

This example describes the esterification of 1-butene with acrylic acid in a discontinuous complete mixture reactor and reveals the effect of the olefin/acrylic acid molar ratio on the conversion of acrylic acid and on the selectivity of 2-butyl acrylate.

14 grams of cationic exchange resin Lewatit SPC118 previously washed with methanol and dried at 105° C. for 24 hours are loaded in a reactor with 300 cm$^3$ of useful working volume and provided with a stirring system. Acrylic acid and liquid 1-butene are feed into the reactor, the system is pressurized to 20 kg/cm$^2$ with nitrogen and heating is begun until a working temperature of 90° C. is reached. The development of the reaction is followed in time just as is observed in the following table, where the conversion of acrylic acid and selectivity of 2-butyl acrylate obtained are shown for an olefin/acrylic acid molar ratio of 3.

| Reaction time (hr) | 0.5 | 1 | 1.5 | 2 | 3 | 4 |
|---|---|---|---|---|---|---|
| Conversion (%) | 97 | 97.5 | 97.4 | 97.2 | 96.5 | 96 |
| Selectivity (%) | 88 | 80 | 76 | 74 | 68 | 62 |

In accordance with the above table, it is possible to obtain a conversion of acrylic acid of 97 % with a selectivity of 2-butyl acrylate of 88 %. The main by-products are C$_8$ olefins produced by dimerization of 1-butene.

EXAMPLE 2

Figure 1:
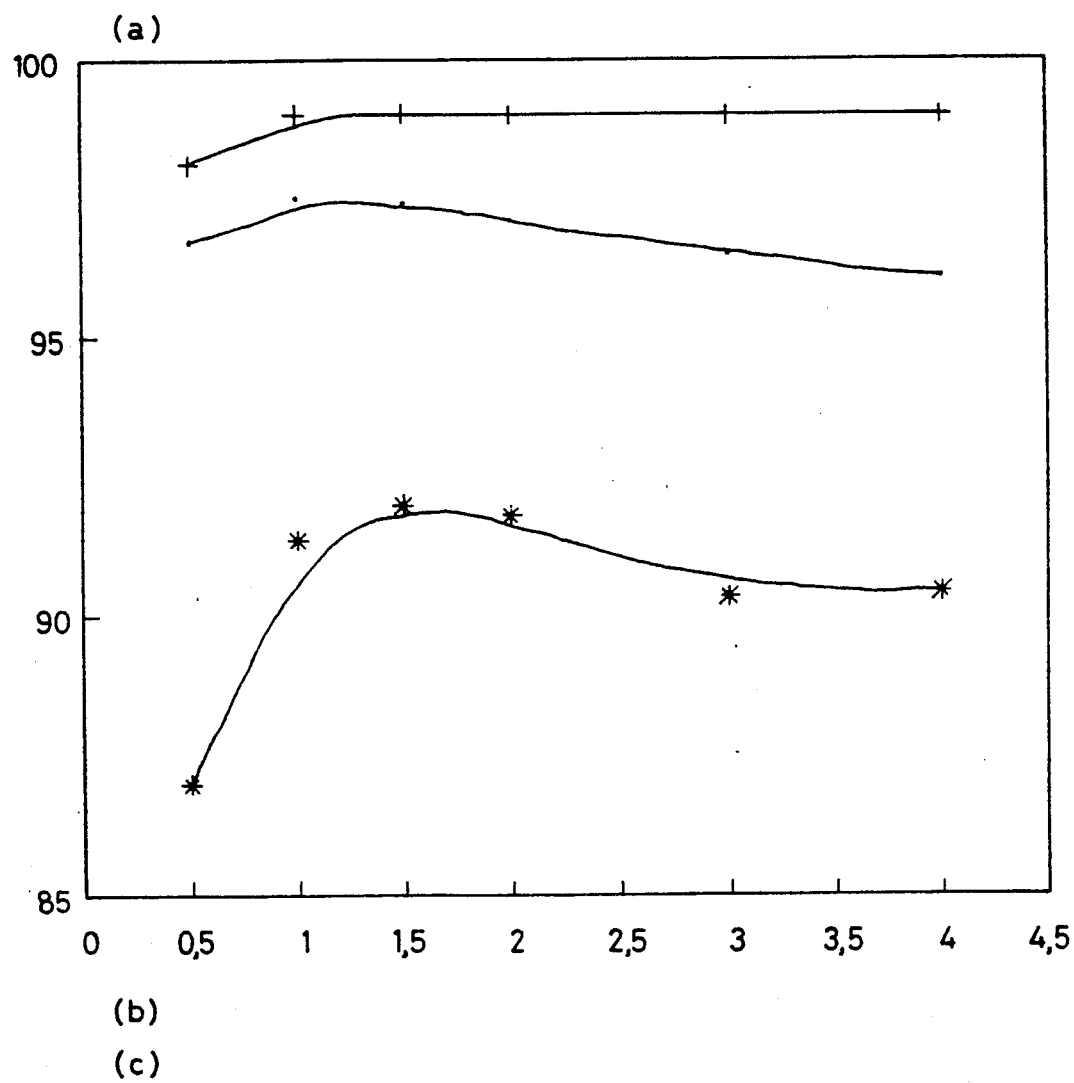
FIG. 1: Graph which represents the effect of the olefin/acrylic acid molar ratio on the conversion of the acrylic acid.

Despite the high conversion obtained in the above example, it is even possible to increase said value, acting upon the olefin/acrylic acid molar ratio. FIG. 1 shows the conversions obtained in three experiments carried out in a similar fashion and under conditions identical to those of Example 1, but under which three different reacting agents molar ratios have been worked at: 1.5, 3 and 5.

It is noteworthy that at higher olefin/acrylic acid molar ratios the conversion of the acid increases, reaching a value of 98.5 % at a molar ratio of 5. From the point of view of selectivity the effect is the opposite, just as is shown in FIG. 2, obtaining the maximum selectivity at an olefin/acrylic acid molar ratio of 1.5.

EXAMPLE 3

This example illustrates the effect of temperature on conversion of acrylic acid and selectivity of 2-butyl acrylate during reactions carried out in a discontinuous stirring tank.

The procedure used is the same as that of Example 1 and the following table shows the results obtained at the three levels of temperature used and at a constant reaction time of 1 hour. The experiments were carried out at an olefin/acrylic acid ratio of 5 moles.

| Temperature (°C.) | 70 | 80 | 90 |
|---|---|---|---|
| Conversion (%) | 83 | 93 | 98.5 |
| Selectivity (%) | 85 | 83 | 70 |

In view of the above table it is observed that the conversion of acrylic acid increases with temperature, reaching at 90° C. a value of 98.5 % and that the effect on selectivity is the contrary to that on conversion, decreasing with temperature.

EXAMPLE 4

This example illustrates esterification of 1-butene with acrylic acid in the presence of a cationic exchange resin when the reaction is carried out in a continuous stirring tank and with internal recirculation.

The reactor with internal recirculation (Berty type) is loaded with 125 cm$^3$ of cationic exchange resin Lewatit SPC118 previously subjected to a dehydration process by washing with methanol and dried at 105° C. A liquid mixture of acrylic acid and 1-butene is continuously fed into the reactor maintaining a total flow of 125 cm$^3$/hr and an olefin/acid molar ratio of 3. Operating under these conditions of LHSV=1 hr$^{-1}$, at a reactor temperature of 87° C. and at a pressure of 20 kg/cm$^2$, the following results have been obtained:

| Acrylic acid | |
|---|---|
| Conversion: | 90.3% |
| Selectivity of 2-butyl acrylate | —100% |
| 1-butene | |
| Conversion: | 47.5% |
| Selectivity of 2-butyl acrylate | 54.4% |

The cationic exchange resin has operated for 20 days continuously without a great loss of initial activity.

We claim:

1. A process for making sec-butyl acrylate comprising:
   reacting acrylic acid and 1-butene in the presence of an ion-exchange resin, said resin containing sulfonic acid groups under the following conditions:
   i) a reaction temperature within the range of 50°–120° C.;
   ii) a reaction pressure within the range of 10–30 kg/cm$^2$;
   iii) a reactant contact time within the range of 0.5–4 hours; and
   iv) a molar ratio of butene to acrylic acid within the range of 0.3 and 10.

2. The process of claim 1 wherein said reaction temperature is within the range between 80° and 110° C.

3. The process of claim 1 wherein said molar ratio is within the range of 1–5.

4. The process of claim 1 wherein said reacting takes place batchwise by contacting said acid, said butene and said resin under agitation.

5. The process of claim 1 wherein said reacting takes place continuously by contacting said acid and said butene with said resin, said resin being immobilized in a stationary bed.

* * * * *